US011058699B2

(12) United States Patent
Lambert et al.

(10) Patent No.: US 11,058,699 B2
(45) Date of Patent: Jul. 13, 2021

(54) METHOD AND COMPOSITIONS FOR INHIBITION OF DOUBLE STRANDED DNA VIRUSES

(75) Inventors: Paul F. Lambert, Madison, WI (US); Shane Pearce, Eau Claire, WI (US); Paul G. Ahlquist, Madison, WI (US); Dohun Pyeon, Greenwood Village, CO (US)

(73) Assignee: WISCONSIN ALUMNI RESEARCH FOUNDATION, Madision, WI (US)

( * ) Notice: Subject to any disclaimer, the term of this patent is extended or adjusted under 35 U.S.C. 154(b) by 0 days.

(21) Appl. No.: 13/000,279

(22) PCT Filed: Jun. 29, 2009

(86) PCT No.: PCT/US2009/049085
§ 371 (c)(1),
(2), (4) Date: Apr. 15, 2011

(87) PCT Pub. No.: WO2010/002804
PCT Pub. Date: Jan. 7, 2010

(65) Prior Publication Data
US 2011/0189258 A1   Aug. 4, 2011

Related U.S. Application Data

(60) Provisional application No. 61/133,676, filed on Jul. 1, 2008.

(51) Int. Cl.
| *A61P 31/20* | (2006.01) |
| *A61K 31/7048* | (2006.01) |
| *A61K 31/52* | (2006.01) |
| *A61K 31/047* | (2006.01) |
| *A61K 31/505* | (2006.01) |

(52) U.S. Cl.
CPC ........ *A61K 31/7048* (2013.01); *A61K 31/047* (2013.01); *A61K 31/505* (2013.01); *A61K 31/52* (2013.01); *C12N 2710/20011* (2013.01); *G01N 2333/025* (2013.01); *G01N 2500/10* (2013.01)

(58) Field of Classification Search
None
See application file for complete search history.

(56) References Cited

U.S. PATENT DOCUMENTS

| 6,159,491 A * | 12/2000 | Durrani ................. 424/430 |
| 2003/0125297 A1 * | 7/2003 | Stewart ............. A61K 31/555 514/46 |
| 2007/0173524 A1 | 7/2007 | Prendergast et al. |

FOREIGN PATENT DOCUMENTS

| CN | 1135332 A * 11/1996 |

OTHER PUBLICATIONS

Garcia-Lopez et al. (Pharm Res. Feb. 2006;23(2):378-83. Epub Jan. 1, 2006).*
Liu et al. (J Cell Biochem. May 2000;78(2):334-49).*
Hainsworth (Cancer, Aug. 1, 2001, vol. 92, No. 3, pp. 642-648).*
Syed (International Journal of STD & AIDS 2000; 11: 371-374).*
Bucknall (Antimicrobal Agents and Chemotherapy, Sep. 1973, p. 294-298).*
Machine translation of Ting (CN1135332A, Nov. 13, 1996).*
De Clercq (TRENDS in Pharmacological Sciences vol. 23 No. 10 Oct. 2002).*
Bucket al. Carrageenan Is a Potent Inhibitor of Papillomavirus Infection. PLoS Pathog, 2006, 2(7): e69.*
International Search Report and Written Opinion Corresponding to PCT/US2009/049085.
Invitation to Pay Additional Fees Corresponding to PCT/US2009/049085.
Culp, T., et al., Keratinocyte-Secreted Laminin 5 Can Function as a Transient Receptor for Human Papillomaviruses by Binding Virions and Transferring Them to Adjacent Cells, Journal of Virology, 2006, 80(18):8940-8950.
Culp, T., et al., Human Papillomaviruses Bind a Basal Extracellular Matrix Component Secreted by Keratinocytes Which is Distinct from a Membrane-Associated Receptor, Virology, 2006, 347:147-159.
Day, P., et al., Establishment of Papillomavirus Infection is Enhanced by Promyelocytic Leukemia Protein (PML) Expression, PNAS, 2004, 101(39):14252-14257.
Evander, M., et al., Identification of the Alpha-6 Integrin as a Candidate Receptor for Papillomaviruses, Journal of Virology, 1997, 71(3):2449-2456.
Fay, A., et al., The Positively Charged Termini of L2 Minor Capsid Protein Required for Bovine Papillomavirus Infection Function Separately in Nuclear Import and DNA Binding, Journal of Virology, 2004, 78(24):13447-13454.
Florin, L., et al., Identification of a Dynein Interacting Domain in the Papillomavirus Minor Capsid Protein L2, Journal of Virology, 2006, 80(13):6691-6696.
Fothergill, et al., Papillomavirus Virus-Like Particles Activate the P13-kinase Pathway Via Alpha-6 beta-4 Integrin Upon Binding, Virology, 2006, 352:319-328.
Payne, E., et al., Human Papillomavirus Type 6b Virus-Like Particles Are Able to Activate the Ras-MAP Kinase Pathway and Induce Cell Proliferation, Journal of Virology, 2001, 75(9):4150-4157.
Van Tine, B., et al., Clonal Selection for Transcriptionally Active Viral Oncogenes During Progression to Cancer, Journal of Virology, 2004, 78(20):11172-11186.
Ferenczy, A. and E. Franco, "Persistent human papillomavirus infection and cervical neoplasia", 2002, The Lancet: Oncology, vol. 3, pp. 11-16.

(Continued)

*Primary Examiner* — Nianxiang Zou
(74) *Attorney, Agent, or Firm* — Quarles & Brady LLP

(57) ABSTRACT

A method of inhibiting double-stranded DNA virus infection is disclosed. In one embodiment, the method involves exposing a papillomavirus to an effective amount of an inhibitor selected from the group of G1, S, G2, and M cell cycle inhibitors. In another embodiment, the method involves administering an inhibitor selected from the group of G1, S, G2, and M cell cycle inhibitors to a susceptible tissue or cell.

20 Claims, 11 Drawing Sheets

Specification includes a Sequence Listing.

(56) References Cited

OTHER PUBLICATIONS

Liu, Y. et al., "Human papillomavirus type 16 E6 and HPV-16 E6-E7 sensitize human keratinocytes to apoptosis induced by chemotherapeutic agents: Roles of p53 and caspase activation", 2000, Journal of Cell. Biochem., vol. 78, No. 2, pp. 334-349.
International Search Report and Written Opinion Corresponding to PCT/US2009/049085, International publication date: Jan. 7, 2010.
Lee et al., "Differential protein expression of etoposide-treated CaSki cervical carcinoma cells", Dec. 1, 2005; retrieved from the Internation Dec. 18, 2009: http://www.koreanmed.or/SearchBasic.php?DT=1&RID=469672.
Garcia-Lopez, et al., "The Systemic Absorption of Etoposide after Intravaginal Administration in Patients with Cervical Intraepithelial Lesions Associated with Human Papillomavirus Infection"; Pharm Res. 2006, 23(2):378-383.
Pyeon, Dohun, et al., "Establishment of Human Papillomavirus Infection Requires Cell Cycle Progression", PLoS Pathogens, Feb. 2009; vol. 5, issue 2, pp. 1-9.
Lacey, Charles J. N., et al. "Chapter 4: Burden and management of non-cancerous HPV-related conditions: HPV-6/11 disease" Vaccine 24S3 (2006) S3/35-S3/41.

* cited by examiner

A

| Primer name | Sequence | Direction | Position |
|---|---|---|---|
| 16E7-U | 5'-AAATGACAGCTCAGAGGAGGAG | Sense | 645-666 |
| 16E7-L | 5'-GAGTCACACTTGCAACAAAAGG | Antisense | 728-749 |
| 16E2-U | 5'-ACTATCCAGCGACCAAGATCAG | Sense | 3464-3485 |
| 16E2-L | 5'-TGTTAAATGCAGTGAGGATTGG | Antisense | 3551-3572 |
| 16E5-U | 5'-TTTGTGTGCTTTTGTGTGTCTG | Sense | 3905-3926 |
| 16E5-L | 5'-AGAGGCTGCTGTTATCCACAAT | Antisense | 3993-4014 |

B

METHOD AND COMPOSITIONS FOR INHIBITION OF DOUBLE STRANDED DNA VIRUSES

CROSS-REFERENCE TO RELATED APPLICATIONS

This application is a U.S. national phase application and claims priority from PCT/US2009/049085 filed Jun. 29, 2009, which claims priority from U.S. provisional application Ser. No. 61/133,676 filed Jul. 1, 2008, which are incorporated by reference in their entirety for all purposes.

STATEMENT REGARDING FEDERALLY SPONSORED RESEARCH OR DEVELOPMENT

This invention was made with government support under CA022443 awarded by the National Institutes of Health. The government has certain rights in the invention.

BACKGROUND OF THE INVENTION

Human papillomaviruses (HPVs) are DNA viruses associated with major human cancers. As such there is a strong interest in developing new means, such as vaccines and microbicides, to prevent HPV infections. Developing the latter requires a better understanding of the infectious life cycle of HPVs.

The HPV infectious life cycle is closely linked to the differentiation state of the stratified epithelium it infects, with progeny virus only made in the terminally differentiating suprabasal compartment. It has long been recognized that HPV must first establish its infection within the stratum basal; however, why this is the case has not been understood. In part it may reflect specificity of expression of entry receptors. However, this hypothesis could not fully explain the differentiation restriction of HPV infection, since many cell types can be infected with HPVs in monolayer cell culture.

Here, we used chemical biology approaches to reveal that cell cycle progression through mitosis is critical for HPV infection. Using infectious HPV16 particles containing the intact viral genome, G1-synchronized human keratinocytes as hosts, and early viral gene expression as a readout for infection, we learned that the recipient cell must enter M phase (mitosis) for HPV infection to take place. Late M phase inhibitors had no effect on infection; whereas, G1, S, G2, and early M phase cell cycle inhibitors efficiently prevented infection. We conclude that, host cells need to pass through early prophase for successful onset of transcription of the HPV encapsidated genes. These findings provide a new understanding for why HPVs initially establish infections in the basal compartment of stratified epithelia. Only this compartment of the epithelia contains cells progressing through the cell cycle, and therefore it is only in these cells that HPVs can establish their infection. By defining a major condition for cell susceptibility to HPV infection, these results also have potentially important implications for HPV control.

Human Papillomaviruses (HPV), which comprise more than 100 genotypes, are the most prevalent sexually transmitted infection and are associated with multiple human cancers including all cervical cancers, many other anogenital cancers, and 25% of head and neck cancers. HPV has unique life cycle which is closely linked to epithelial differentiation of skin keratinocytes, with initial infection occurring only in the undifferentiated proliferating basal compartment of epithelium and progeny virus production only in the terminally differentiated suprabasal compartment. So far, little is known about how host cells restrict the HPV life cycle to specific stages of skin development. Here, in an effort to screen HPV small molecule inhibitors, we revealed that cell cycle progression through mitosis is critical for the establishment of HPV infection. In addition, our further chemical genetic dissection of this process showed that early steps of mitosis are required for HPV infection and early gene expression. Our new finding could explain why HPV only infects undifferentiated proliferating cells and provide new leads for the development of preventive and therapeutic strategies against HPV infection.

Needed in the art is a better understanding of the infectious life cycle of HPVs and better prevention methods.

SUMMARY OF INVENTION

In one embodiment, the present invention is a method of inhibiting double-stranded DNA virus infection. It relies on the inventor's observations that G1, S, G2, and M cell cycle inhibitors inhibit double-stranded DNA viruses.

In a first aspect, the present invention is a method of inhibiting double-stranded DNA virus infection. In one embodiment of the first aspect the method comprises the steps of (a) identifying an individual in danger of viral infection, and (b) exposing tissues or cells of the individual that are susceptible to virus infection to an effective amount of a viral inhibitor, wherein the inhibitor is selected from the group of G1, S, G2, and M cell cycle inhibitors.

In different embodiments of the first aspect, the virus is a papovavirus, HPV, high risk HPV, low risk HPV, or HPV 16. In other embodiments of the first aspect, the inhibitor is selected from the group consisting of etoposide, aphidicolin, 5FU, and purvalanol, and the tissue or cells are selected from the group consisting of vulvovaginal tissues and cells, rectal tissues and cells, oral cavity tissues and cells, and oral pharynx tissue and cells. In still other embodiments of the first aspect, and effective amount of a viral inhibitor selected from the group of G1, S, G2, and M cell cycle inhibitors is a concentration of at least 0.1 µM. In another embodiment, the concentration is at least 1.5 µM.

In a second aspect, the present invention is a composition comprising an effective amount of a viral inhibitor selected from the group of G1, S, G2, and M cell cycle inhibitors and a pharmaceutically acceptable carrier, wherein the viral inhibitor is effective for inhibiting papillomavirus infection.

In a third aspect, the present invention is a composition comprising an effective amount of a viral inhibitor selected from the group of G1, S, G2, and M cell cycle inhibitors and mixtures thereof and a product designed for application in the vaginal or rectal areas.

In one embodiment of the second aspect, the product designed for application in the vaginal or rectal areas is a spermicide, lubricant, cream, ointment, solution, powder, impregnated tampon, rectal or vaginal suppository, pessary, or implant.

In a third aspect, the present invention is a composition comprising an effective amount of a viral inhibitor selected from the group of G1, S, G2, and M cell cycle inhibitors and mixtures thereof and a product designed for application by inhalation into the respiratory system.

In one embodiment of the third aspect, the product designed for application by inhalation into the respiratory system is a spray, aerosol, or foam.

BRIEF DESCRIPTION OF THE DRAWINGS

(FIG. 2A) After 24 hour incubation in serum-free Dulbecco's Modified Eagle's Medium (DMEM), HaCaT cells were infected with HPV pseudovirion hpv16wpA-RL and Renilla Luciferase (RL) activity was measured after 2 days. For serum conversion, serum-free DMEM was replaced with 10% fetal bovine serum (FBS)/DMEM before virus inoculation. The expression value is shown as % infectivity to untreated hpv16wpA-RL inoculation. The columns represent the mean, the bars represent the standard deviation. (FIG. 2B) Flow cytometry was performed to confirm cell cycle arrest by serum starvation. The solid line indicates the HaCaT cells incubated with serum-free DMEM for 24 hours and the gray shaded area indicates control HaCaT cells in DMEM with 10% FBS.

(FIG. 3A) HaCaT cells were synchronized with aphidicolin (sets 1, 2, 4, and 5) and etoposide (set 3) 24 hours before hpv16wpA-RL inoculation. Cell cycle progression was released in set 1 and kept blocked in set 2 and 3 using aphidicolin and etoposide, respectively. In set 4, cell cycle progressed through S phase but arrested at G2 phase by switching the compounds in medium from aphidicolin to etoposide. In set 5, cell cycle was released for 20 hours to progress through M phase and arrest at G2 phase by etoposide addition. Experimental protocols are shown as diagrams. Solid arrows and dotted arrow indicate aphidicolin and etoposide in cell culture medium, respectively. Histograms show the results of flow cytometry analysis following propidium iodide staining at 0, 24, and 48 hour time points using a cell cycle analysis program of FlowJo. (FIG. 3B) The reporter RL activity was measured by Renilla Luciferase Assay System (Promega).

(FIG. 5A) HaCaT cells were treated with different concentrations of monastrol, and hpv16wpA-RL infectivity was assessed as above. Dotted line is for mock-infected cells. (FIG. 5B) Cell cycle arrest at M phase by monastrol (100 μM) was confirmed using flow cytometry. Histograms indicate the cell cycle status of DMSO and monastrol-treated cells, respectively.

(FIG. 6A) 293T cells were treated with a CDK1 inhibitor, purvalanol A (3, 6, and 12 μM) and infected with hpvSEAP. SEAP activity was assayed after 48 hours incubation as described in the Experimental Procedures section in Example I. p<0.05, significantly different from the dimethyl sulfoxide (DMSO) control. The columns represent the mean, the bars represent the standard deviation. (FIG. 6B) Cell cycle arrest at M phase by purvalanol A (12 μM) is shown. Histograms indicate the cell cycle status of DMSO and purvalanol A-treated cells, respectively.

(FIG. 7A) After 24 hour synchronization with aphidicolin and 4 hour treatment with etoposide or aphidicolin (3 μM each), 293T cells were infected with hpv16wpA-RL or an influenza virus vector in which hemagglutinin and neuraminidase open reading frames in viral RNA were replaced with those of vesicular stomatitis virus glycoprotein and RL, respectively (Watanabe et al., J. Virol. 77: 10575-10583). (FIG. 7B) After 24 hour synchronization in serum-free DMEM, HaCaT cells were infected with hpv16wpA-RL and the RL-expressing influenza virus as in FIG. 7A in the presence or absence of FBS. RL activity was measured after 48 hours, as described in the Experimental Procedures section in Example I, normalized to RL activity in equivalently inoculated cells maintained in 10% FBS and expressed in the histograms as % infectivity. The columns represent the mean, the bars represent the standard deviation.

(FIG. 11A) Oligonucleotide primers were designed using the Primer3 primer design program. (FIG. 11B) The HPV genomic position of each primer is indicated by an arrow.

DETAILED DESCRIPTION OF THE INVENTION

A. In General

Figure 1:
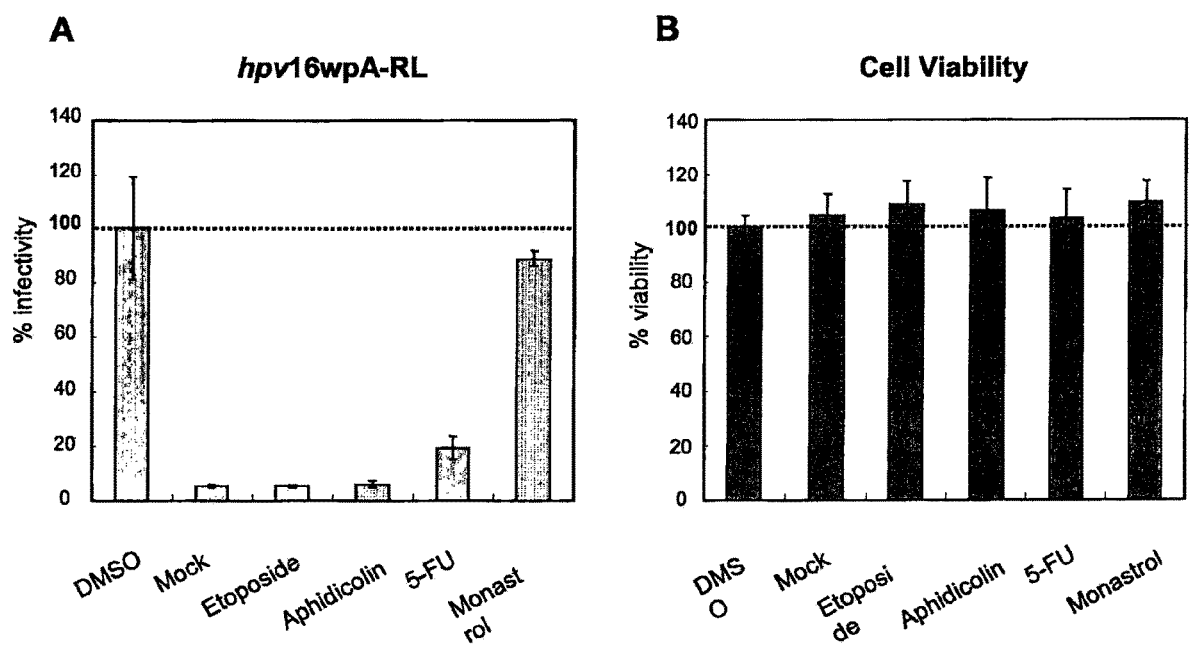
FIG. 1. Selected cell cycle inhibitors abrogate HPV infection. The reporter RL activity (FIG. 1A) and cell viability (FIG. 1B) were measured by Renilla Luciferase Assay System (Promega) and CellTiter-Glo Luminescent cell viability assay (Promega), respectively. Human keratinocyte HaCaT cells were inoculated with HPV16 LCR-driven RL containing pseudovirions hpv16wpA-RL after 4 hours of pre-treatment with 3 μM of each compound, and reporter expression/cell viability were scored 48 hours later. The expression value is shown as viability to untreated cells with hpv16wpA-RL.

Anogenital HPVs are the most common sexually transmitted pathogens, and the chief cause of anogenital cancers including cervical, vaginal, vulvar, penile, and anal cancers. Recently developed vaccines may provide some level of protection against a subset of these viruses, however, their use is still limited due to cost, social acceptance, and access to health care providers. In one embodiment, the present invention is a method of inhibiting DNA virus infection comprising the steps of identifying an individual in danger of viral infection and exposing tissues or cells of the individual that are susceptible to papillomavirus virus infection to an effective amount of a viral inhibitor, wherein the inhibitor is selected from the group of G1, S, G2 and M cell cycle inhibitors.

By "effective amount" we mean an amount effective to inhibit HPV infection preferably 95%, more preferably 99%, and most preferably 100%.

In a preferred embodiment, the inhibitor of the present invention is selected from the group consisting of etoposide, aphidicolin, 5FU and purvalanol.

B. Inhibited Viruses

In one broad embodiment, the present invention is a method and composition for inhibition of papovaviruses, such as human papillomaviruses (HPVs). In one version of the present invention, the method would be used to inhibit all HPVs.

In another embodiment, the invention would be used to inhibit high risk HPVs, such as HPV16, 18, 31, 33, 35, 39, 45, 51, 52, 53, 56, 58, 59, 66, 68, 70, 73, 82, and 83. In a specific embodiment, the invention is used to inhibit HPV 16. In another embodiment, the invention could be used to inhibit low oncogenic risk HPVs such as HPV6, 11, 40, 42, 43, 44, 54, 61, 70, 72, 81, and 89. In still another embodiment, the invention is used to inhibit combinations of HPV genotypes.

In another embodiment, the present invention is used to inhibit double strand DNA viruses. By "double strand DNA virus" we mean all other papillomaviruses and other viruses that require cell cycle progression for infection and/or replication such as polyomaviruses, herpesviruses, and adenoviruses.

In yet another embodiment, the present invention is used to inhibit retroviruses. By "retrovirus" we mean both simple and complex retroviruses.

HPVs are DNA viruses are associated with major human cancers. We envision that other oncogenic viruses, particularly oncogenic DNA viruses and oncogenic retro viruses, would be excellent candidates for the present invention.

C. Cell Cycle Progression

The HPV life cycle is closely linked to differentiation of the stratified epithelium the virus infects. HPV only infects proliferating basal cells, and progeny virions only produce as daughter cells terminally differentiate. However, the crucial early steps of HPV infection from cell binding through nuclear delivery of viral DNA for early gene expression remain poorly understood, and the basis of HPV infection specificity for dividing cells is unknown.

In the Examples below we used chemical biology approaches to reveal that cell cycle progression through mitosis is critical for HPV infection. Further analysis showed that, after HPV attachment and entry, recipient cells must pass through early prophase, but not late prophase and metaphase, to allow transcription of HPV-encapsidated genes in the nucleus. These requirements parallel those of simple retroviruses that enter via nuclear envelope breakdown (NEBD). The results were experimentally distinct from those of influenza virus, which uses active transport through nuclear pores to deliver its genome to intact nuclei.

Therefore, the inventors propose the use of G1/S and G2/M inhibitors for viral inhibition.

D. Preferred Inhibitors

The example below discloses the elucidation of criteria for preferred antiviral compounds. Example I demonstrates that cell cycle progression through mitosis is critical for HPV infection. Our analysis showed that recipient cells must pass through early prophase but not late prophase and metaphase to allow transcription of HPV encapsidated genes in the nucleus.

Thus, we have learned that inhibitors of the cell cycle at G1/H and G2 stage are effective antivirals. These small molecules target multiple cyclin-dependent kinases such as CDK1 and CDK2. The examples below show that aphidicolin and etoposide significantly and consistently inhibit HPV 16. Therefore, in one embodiment of the present invention the cell cycle inhibitors are aphidicolin or etoposide. In another embodiment, the cell cycle inhibitor is an G1/S and/or G2/M inhibitor. Other examples of G1/S and G2/M inhibitors are as follows:

G1/S inhibitors: Aphidicolin, 5-Flourouracil, Daidzein, Netropsin, XK469, Sobuzoxane, Amethopterin, PD 0183812, Fascaplysin, L-Mimosine- G2/M inhibitors: Etoposide, Purvalanol, Apigenin, Indirubin-3'-oxime, Staurosporine, Scytonemin, Camptothecin. BI 2536, and CGP-74514A.

G1/S and G2/M inhibitors: Olomoucine, Roscovitine, NU2058, NU6027, Flavopiridol, and Butyrolactone.

E. Tissues And Cells

In one embodiment, the present invention is a method of inhibiting viruses and blocking the establishment of viral infection. Preferably, the virus is either HPV or one of the viruses discussed above. In a preferred embodiment of the present invention, one would apply the inhibitor to a skin surface area susceptible to viral infection.

In one embodiment of the present invention, one would administer an inhibitor selected from the group consisting of G1/S and GM/2 inhibitors to a susceptible tissue or cell. By "susceptible tissue or cell", we mean a tissue or cell that is capable of infection by a double strand DNA virus, preferably a papillomavirus, more preferably HPV. So far, the only confirmed way of HPV transmission is direct and indirect skin contact, including sexual activities. However, as HPV also infects mouth and throat tissue and recent studies showed some lung cancers are associated with HPV infection, HPV transmission might be much more complicated than we know now. Additional preferred tissues would be those of the oral cavity and oral pharynx.

F. Preferred Methods

In one embodiment, if one wished to prevent HPV infection, one would add the inhibitor to a spermicide, lubricant, or other product designed for application in the vaginal area. In another preferred embodiment, the pharmaceutical composition may be selected from the group consisting of rectal or vaginal suppositories, ointments, solutions, powers, and impregnated tampons. In another embodiment of the present invention, the pharmaceutical composition is administered as a spray, aerosol, or foam.

Vaginal or vulvovaginal delivery of a medication may be by a device, such as disclosed in U.S. Ser. No. 11/763,085 and 11/454,604. A "vulvovaginal surface" herein denotes any external or internal surface of the female genitalia, including mucosal surfaces in the vaginal cavity and non-mucosal surfaces of the vulva and immediately surrounding areas of skin. In some embodiments, the composition is more specifically adapted for application to a vaginal mucosal surface, and an external phase of the composition is bioadhesive to such a surface.

A composition used in methods of the invention can be in any suitable form that is adapted for vulvovaginal administration. For intravaginal administration, suitable forms include a vaginal cream, tablet, suppository, pessary or implant, but in particular embodiments, the composition is in the form of a vaginal cream.

The composition can be administered topically to external surfaces of skin surface, preferably the vulva and/or to surrounding areas of skin. In addition or alternatively, the composition can be administered intravaginally. In one embodiment, the composition is a vaginal cream, i.e., a semi-solid formulation adapted for administration to vaginal mucosal surfaces.

A vaginal cream for use according to methods of the invention can be administered to contact a mucosal surface in the vaginal cavity by means, for example, of an applicator that is optionally pre-filled with a single unit dosage amount of the cream. With the patient optionally in a supine position, the tip of the applicator can be gently inserted high in the vagina, for example in the posterior vaginal formix, and the cream can be released through the tip by pushing on a plunger of the applicator.

In some embodiments anal or rectal delivery of the inhibitor would be preferred. Suitable formulations for rectal administration include, for example, suppositories, which consist of the packaged inhibitor with a suppository base. Suitable suppository bases include natural or synthetic triglycerides or paraffin hydrocarbons. In addition, it is also possible to use gelatin rectal capsules which consist of a combination of the packaged inhibitor with a base, including, for example, liquid triglycerides, polyethylene glycols, and paraffin hydrocarbons. Another option is the use of penile lubricants.

If one is concerned about protection about other categories of viruses, one would apply the inhibitor as follows: For respiratory viruses (e.g. adenoviruses) application may be via inhaled mist. For enteric viruses, delivery would be via oral route. For other viruses, such as arthropod borne viruses, systemic delivery might be appropriate.

F. Dose And Concentration

In one embodiment of the present invention, determining a proposed human dose would first involve testing in the mouse model doses in existing or modified vehicle formulations currently used in vaginal/penile lubricants and contraceptive jellies/creams. If necessary, one would make tolerated modifications to the drugs to improve their solubility in these vehicle formulations.

In another embodiment of the present invention, the proposed human dose is a compound concentration of at least 1.5 µM. In a preferred embodiment, the concentration is at least 0.1 µM.

Example I

Establishment of Human Papillomavirus Infection Requires Cell Cycle Progression

The tight link between keratinocyte differentiation and the HPV life cycle has made large scale production of mature infectious HPV particles difficult, greatly restricting studies of the mechanisms of natural HPV infection (Dollard S. C. et al. (1992) OFF. Genes Dev. 6: 1131-1142; Meyers C. et al., (1992) Science 257: 971-973). Recently developed transfection methods that generate large yields of virus particles and efficient encapsidation of target plasmids as large as the full length ~8 kb HPV genome have overcome this limitation (Buck C. B. et al., (2004) J. Virol 78: 751-757; Pyeon D, et al., (2005) Proc. Nat'l Acad. Sci. USA 102: 9311-9316. Epub 2005 June 9315).

This technique provides a genetically modifiable, high yield source of infectious HPV and HPV pseudoviruses expressing reporter genes for studies of different early steps of HPV infection including virion binding, endocytosis, uncoating of the virion capsid, release from the endosome, trafficking to the nucleus, delivery of viral DNA to the nucleus, and transcription of encapsidated genes.

To define the pathways and mechanisms involved in these early steps of HPV infection, we tested approximately 5,000 bioactive compounds with known mechanisms of action for effects on the entry of HPV capsids containing reporter genes or the full HPV genome, and identified a subset of cell cycle inhibitors that completely blocked wild type HPV infection. Our further studies showed that cell cycle progression through early stages of mitosis is critical for successful HPV infection. These findings reveal new insights into the mechanism by which HPV infects cells and provide one reason why HPV infects only undifferentiated, proliferating cells. These results also provide new leads for developing preventative and therapeutic strategies against HPV infection.

Results

Cell cycle inhibitors block HPV infection. To identify mechanistic pathways and informative modulators of HPV infection, we tested nearly 5,000 compounds in known bioactive molecule libraries Prestwick (Prestwick Chemicals) and LOPAC (Library of Pharmacologically Active Compounds, Sigma), with HPV pseudovirions containing an SV40 promoter-driven secreted alkaline phosphatase (SEAP) reporter gene (hpvSEAP). 293T cells were infected with wild type HPV16 after 4 hours of pre-treatment with 3 µM of each compound or with 1:100 dilution of neutralizing antibody (H16.7E). Total RNA was extracted after 48 hours, and expression levels of HPV16 E1 ^E4 RNA transcripts were measured by qRT-PCR using E7, E2, and E5 sequence specific primers.

High activity effectors identified in this assay were retested in a second infectivity assay using HPV pseudovirions containing Renilla luciferase driven by the natural HPV16 promoter (hpv16wpA-RL) to exclude false positive compounds that may directly affect the SV40 promoter or alkaline phosphatase (data not shown). Secondary screens performed in HaCaT cells, an immortalized line of human keratinocytes, which are natural host cells for HPV infection, confirmed the validity of the hits, as indicated below.

Among the confirmed hits identified in the primary screen were cell cycle inhibitors etoposide (Pedrali-Noy G. et al., (1980) Nucleic Acids Res. 8:377-387) and aphidicolin (Lock R. B. and Ross W. E. (1990) Cancer Res. 50:3761-3766) showed the most significant and consistent inhibition on HPV infection in 293 cells both using HPV16 pseudoviruses expressing SEAP or Renilla luciferase reporter genes, or using intact infectious HPV16 virus in which we scored for early gene expression (FIG. 1). The levels of inhibition achieved with these drugs was greater than that achieved with neutralizing antibody to HPV16 (FIG. 1A), and were specific to virally expressed gene as the drugs had no effect on cellular β-actin expression (FIG. 1B).

Figure 8:
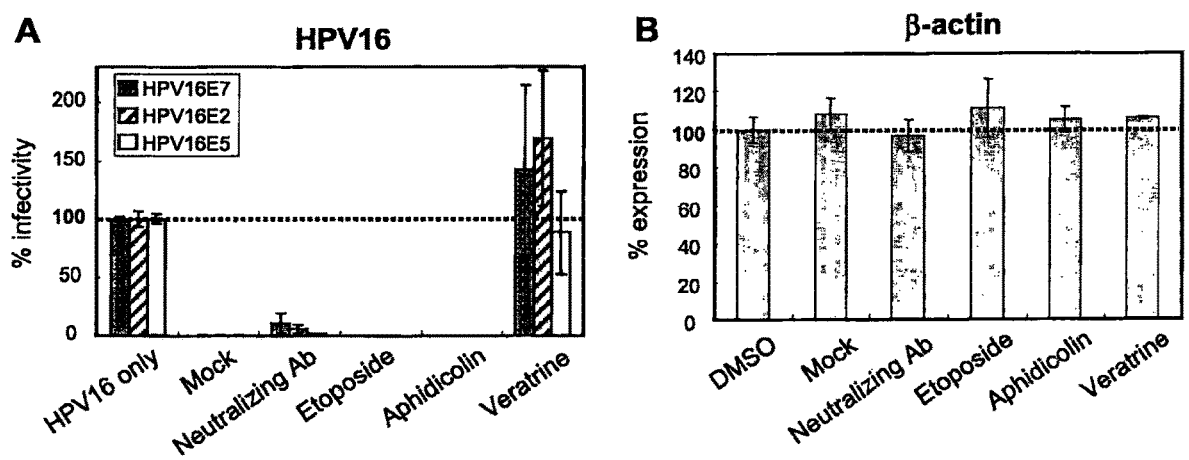
FIG. 8. Selected cell cycle inhibitors abrogate HPV infection. HPV16 early gene (FIG. 8A) and β-actin expression (B) was measured by quantitative RT-PCR. 293T cells were inoculated with wild type HPV16 after 4 hours of pre-treatment with 3 μM of each compound or with 1:100 dilution of neutralizing antibody (H16.7E). Total RNA was extracted after 48 hours, and expression levels of HPV16 RNA transcripts were measured by qRT-PCR using E7, E2, and E5 sequence specific primers (FIG. 11). The expression value is shown as % infectivity or % expression to untreated cells infected with HPV16. We could not detect any signal above the background in reverse transcriptase-negative controls, indicating that only nRNA expressed from infected virus could be detected (data not shown). Due to different characteristics of each primer set, we observed slight differences in the quantity of mRNAs detected in the same sample with different primer pairs. Those differences, while not statistically significant, could reflect differences in the efficiency of each primer pair amplifying different subsets of viral early mRNAs. Veratrine, and alkaloid drug, was one of many small molecule compounds for the secondary screens. The neutralizing antibody (H16.7E, provided by Neil Christensen at the Pennsylvania State University, Hershey, Pa.) was used as a positive control for HPV infection inhibition.

Our further testing with wild type HPV16 virion infection of 293T cells showed that aphidicolin and etoposide blocked HPV16 gene expression even more efficiently than a neutralizing antibody (FIG. 8A), while cellular β-actin expression was not affected (FIG. 8B). We examined cell cycle status using flow cytometry and found that 3 μM aphidicolin or etoposide, which block HPV infection, arrested cell cycle progression at G1/S and G2 phases, respectively (data not shown), in keeping with their known mechanisms of action (Pedrali-Noy et al., Nucleic Acids Res. (1980) 8: 377-387; Lock et al., Cancer Res. (1990) 50: 3761-3766).

In the more physiologically relevant HaCaT cells, these two drugs along with another cell cycle inhibitor 5-fluorouracil (5-FU) (Lewin F. et al., (1987) Acta Oncol. 26:125-131), all were very robust in identifying infectivity (FIG. 1A) at concentrations that did not have any effect on cell viability (FIG. 1B). These results demonstrate that the original screen, which was done in 293T cells, was successful in identifying drugs that can inhibit HPV infection in a more relevant cell type. More importantly our results suggested that the cell cycle is critical for HPV infection.

Next, we arrested cell cycle using a non-chemical method with serum starvation. HaCaT cells incubated in serum free medium showed complete cell cycle arrest and significant inhibition of HPV infection (FIG. 2A) in efficient cell cycle arrest at G1 phase (FIG. 2B). However, when cell cycle was released upon HPV inoculation, HPV infection was not inhibited, but enhanced about two-fold. These results consistently indicate that cell cycle progression is necessary for HPV early infection and viral gene expression.

Figure 9:
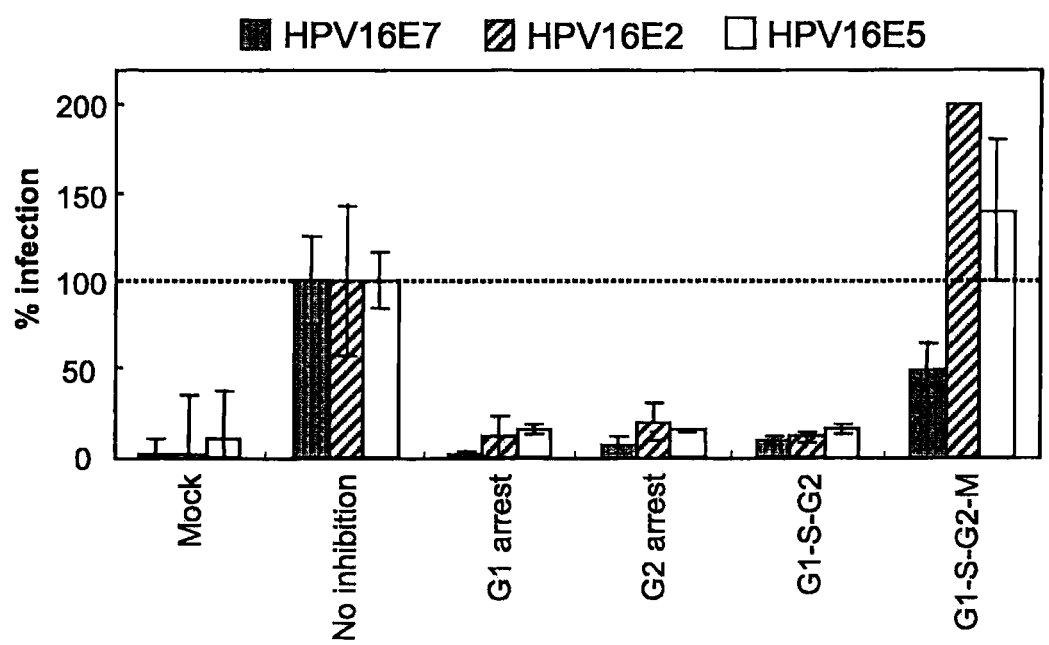
FIG. 9. Cell cycle progression through M phase is critical for HPV infection. 293T cells were synchronized with aphidicolin (sets 1, 2, 4, and 5) and etoposide (set 3) 4 hours before wild type HPV16 inoculation (see FIG. 3). Cell cycle progression was released in set 1 and kept blocked in sets 2 and 3 using aphidicolin and etoposide, respectively. In set 4, cell cycle progressed through S phase, but arrested at G2 phase by switching the compounds in medium from aphidicolin to etoposide. In set 5, cell cycle was released for 20 hours to progress through M phase and arrest at G2 phase by etoposide addition. Wild type HPV16 gene expression was measured from total RNA extracts as indicated in FIG. 8 and in the Experimental Procedures section in Example I.
Figure 10:
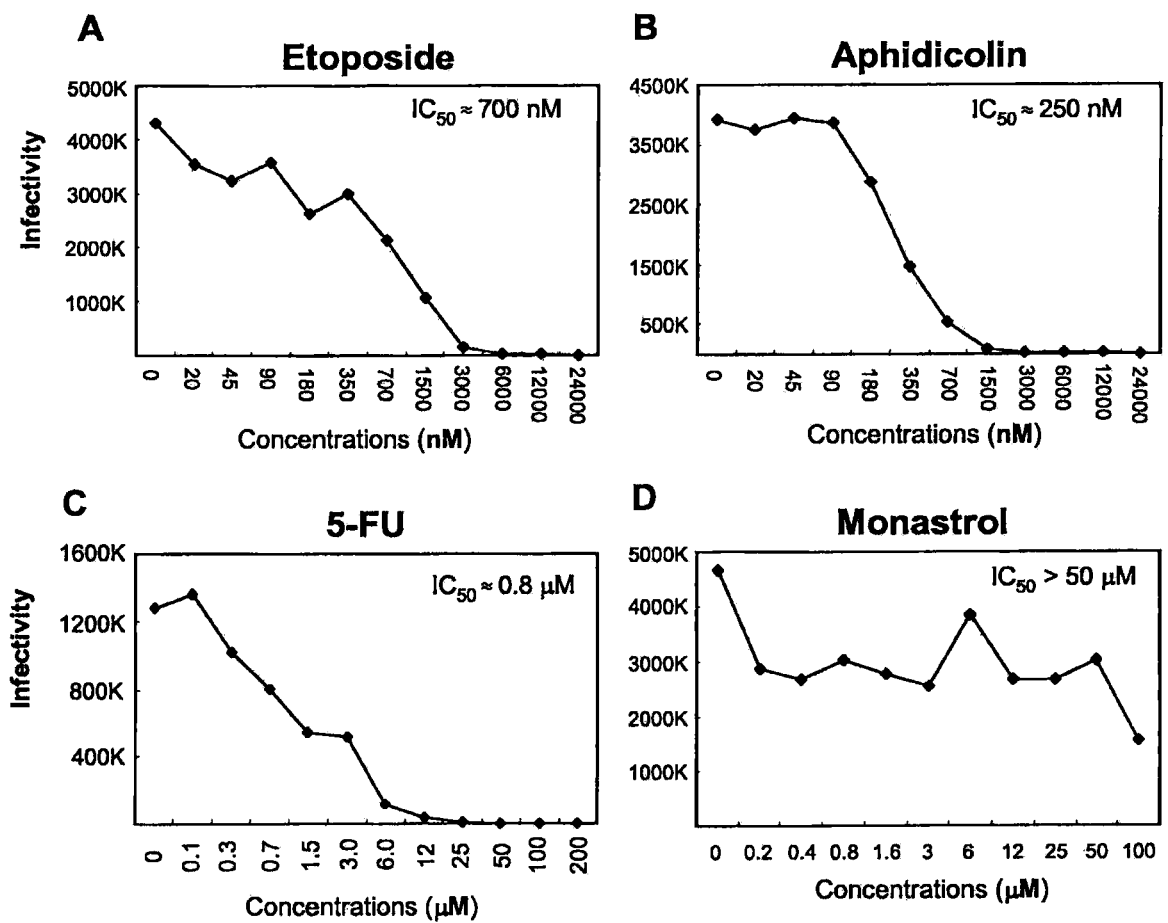
FIG. 10. Dose-dependent inhibition response of HPV infection by cell cycle inhibitors. Shown are results from infection experiments in human keratinocyte HaCaT cells monitoring the efficiency of infection by HPV16 LCR-driven Renilla luciferase containing pseudovirion hpv16wpA-RL in the absence [0 uM, vehicle only] or increasing concentrations [0.02 to 24 uM for etoposide (A) and aphidicolin (B); 0.1 to 200 uM for 5-FU (C); and 0.2 to 100 uM for monastrol(D)]. The Y axis is the infectivity by luminescence as a function of drug concentration (X axis). All data points represent the average of values from triplicate samples.
Figure 11:
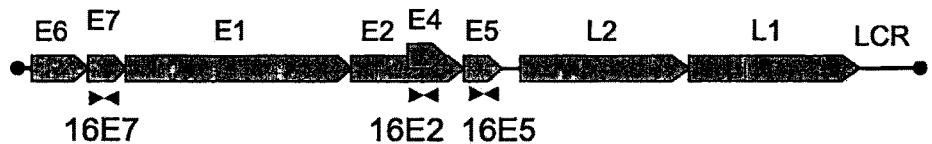
FIG. 11. Quantitative PCR primers of HPV16 early genes.

Cell cycle progression through mitosis is critical for HPV infection. To define which cell cycle step(s) is critical for early HPV infection, we synchronized HaCaT cells with aphidicolin or etoposide and then tightly controlled cell cycle progression. In the first set of the experiments (indicated as No inhibition; FIGS. 3A and 3B), cells were synchronized in G1 phase with a 24 hour aphidicolin treatment, inoculated with hpv16wpA-RL virions, and then 4 hours later, released by removing aphidicolin from the culture medium. After 48 hour incubation, the infected HaCaT cells expressed high levels of RL. The reporter gene expression levels under these "no inhibition" positive control conditions were set to 100% infection and used to normalize the early gene expression levels from the other experimental conditions (FIG. 9).

Figure 3:
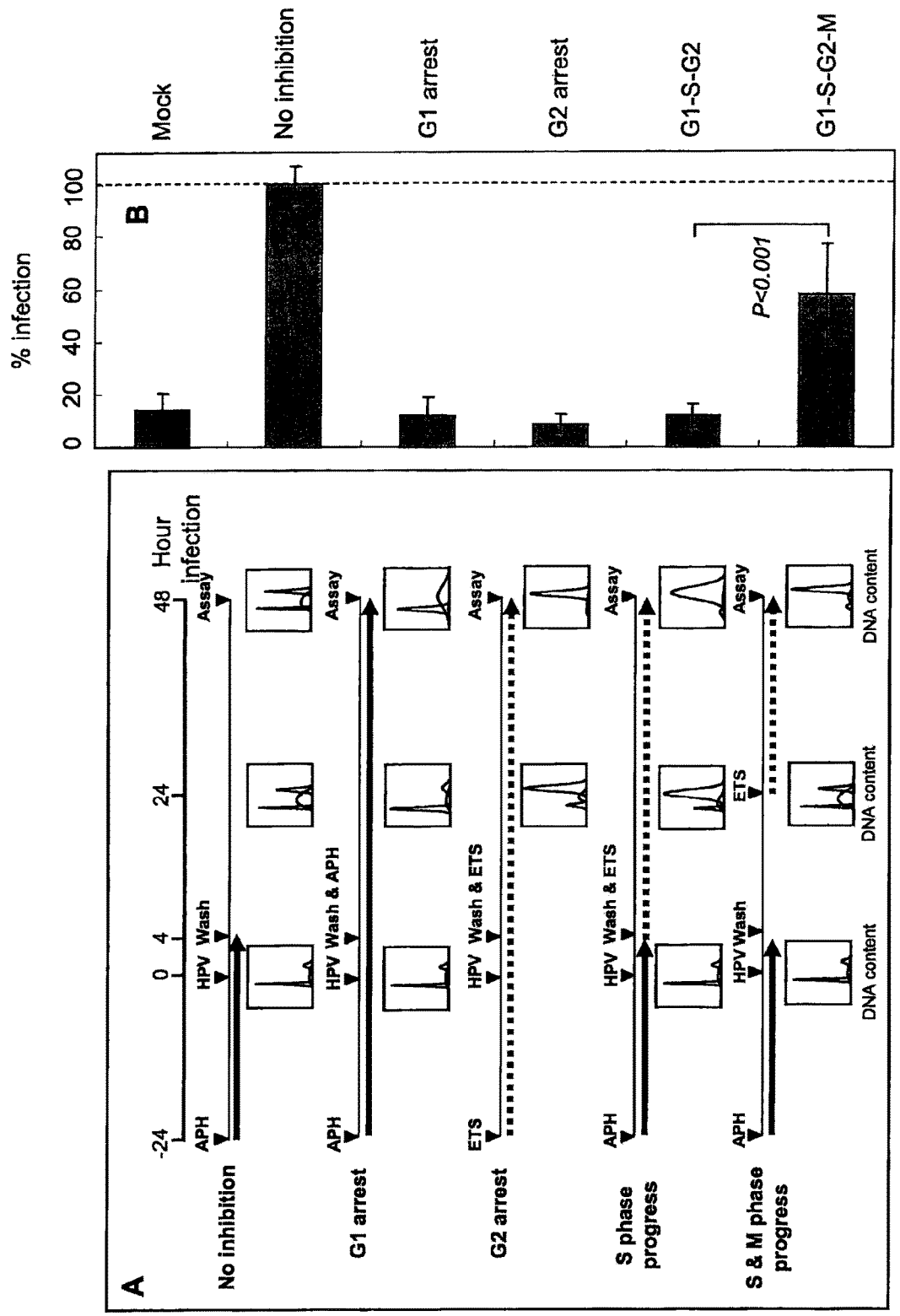
FIG. 3. Cell cycle progression through M phase is critical for HPV infection.

In the second (G1 arrest; FIGS. 3A and 3B) and third (G2 arrest; FIGS. 3A and 3B) conditions used, cells were treated with either aphidicolin or etoposide for 24 hours, after which hpv16wpA-RL virions were added. The cell cycle was blocked at G1/S and G2 by aphidicolin and etoposide, respectively, and HPV infection was significantly and consistently inhibited under both conditions (FIGS. 3A and 3B). These conditions were the same as used in FIG. 1, and the flow cytometric analyses shown in FIG. 3 confirmed effective cell cycle block by aphidicolin and etoposide at the concentrations used in FIG. 1.

In the fourth condition (S phase progress; FIGS. 3A and 3B), we synchronized the cells in G1/S phase by 24 hour aphidicolin treatment, then added hpv16wpA-RL virions and, four hours later, replaced aphidicolin with etoposide. When aphidicolin was replaced by etoposide, cell cycle progressed from G1 arrest through S phase to G2 arrest, allowing us to test whether S phase progression supports HPV early infection. However, this experiment showed no difference in HPV gene expression with G1/S or G2 arrest by aphidicolin and etoposide (FIGS. 3A and 3B).

In the fifth condition (S & M phase progress; FIGS. 3A and 3B), after 24 hour synchronization and subsequent hpv16wpA-RL virion addition, the cell cycle was released for 20 hours, followed by cell cycle arrest in G2 phase with etoposide, allowing the cells to progress through one complete round of the cell cycle, including M phase. Interestingly, one round of M phase progression was sufficient for HPV16 infection and gene expression (FIGS. 3A and 3B).

Figure 2:
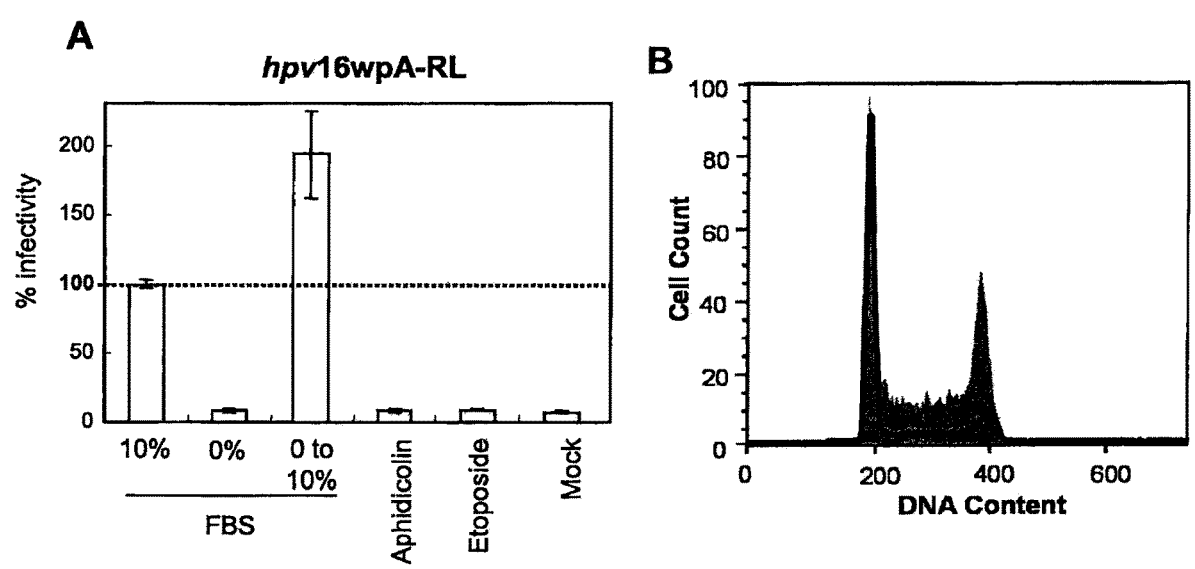
FIG. 2. Cell cycle arrest by serum starvation abrogates HPV infection.
Figure 4:
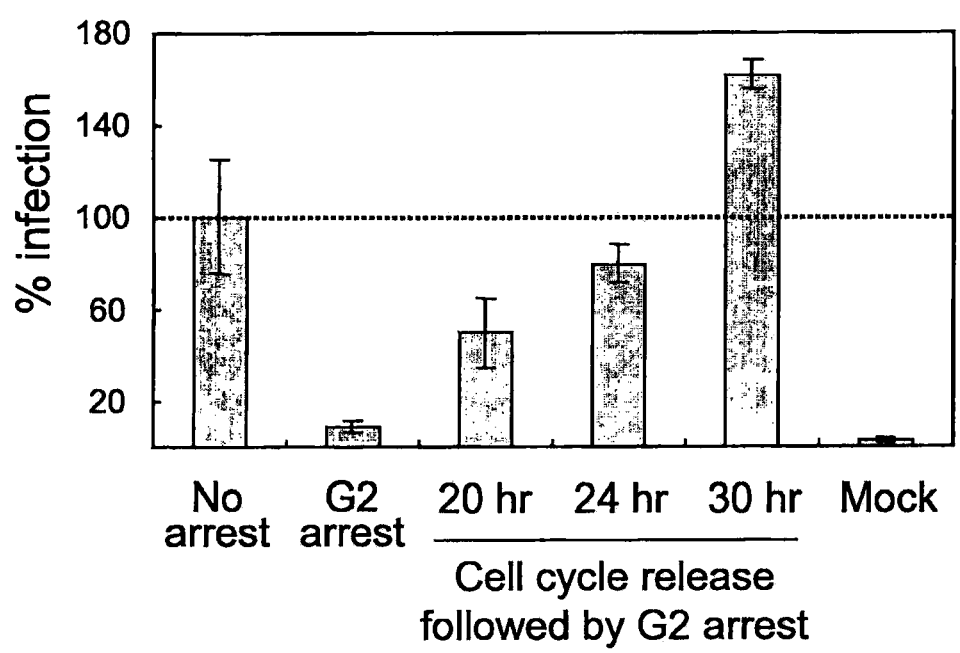
FIG. 4. Cell cycle progression through M phase is critical for HPV infection. Cell cycle release after 24 hours G1 arrest was extended to 24 and 30 hours before G2 arrest by etoposide. Expression of HPV16 early RNA transcripts was measured using E7 specific primers. The columns represent the mean, the bars represent the standard deviation. We could not detect any signal above the background in reverse transcriptase-negative controls, indicating that only mRNA expressed from infected virus could be detected (data not shown).

Interestingly, one round of M phase progression was sufficient for HPV infection and gene expression (FIGS. 3A and 3B). Our further testing with wild type HPV16 virions confirmed that one round of cell cycle progression through M phase is sufficient for HPV early gene expression (FIG. 2). These results imply that cell cycle progression through mitosis is critical for early steps of HPV infection. Consistent with this premise, HPV gene expression levels were further enhanced when the cell cycle was released for progressively longer periods before G2 arrest, eventually reaching levels well above the control "no arrest" conditions (FIG. 4). This suggests that G2 arrest might provide better host cell environment for viral gene expression once the virus enters nucleus.

Figure 5:
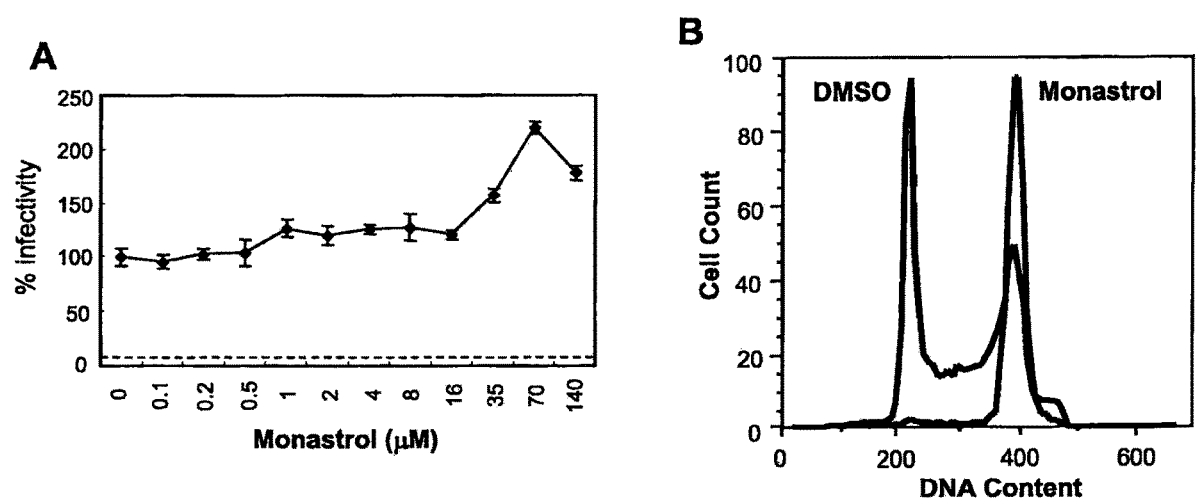
FIG. 5. Late M phase arrest does not affect HPV infection.

Early prophase, but not late prophase or metaphase, is critical for HPV early infection. To define further the states of mitosis and associated cellular functions that are not required to support HPV early infection, we tested monastrol (Mayer et al., Science (1999) 286:971-974), which inhibits mitotic spindle formation during late prophase and metaphase in early to mid mitosis. Interestingly, monastrol, which induced cell cycle arrest in M as expected (FIG. 5B) showed no inhibitory effect on HPV infection in HaCaT cells (FIG. 5A). At high concentrations of monastrol, there was a slight, but reproducible increase in HPV infectivity. Thus, HPV infection can efficiently arise in cells inhibited in late prophase/metaphase. These results, taken together with those in FIG. 3 narrowed down the critical stage of the cell cycle for HPV infection to likely be early prophase.

Figure 6:
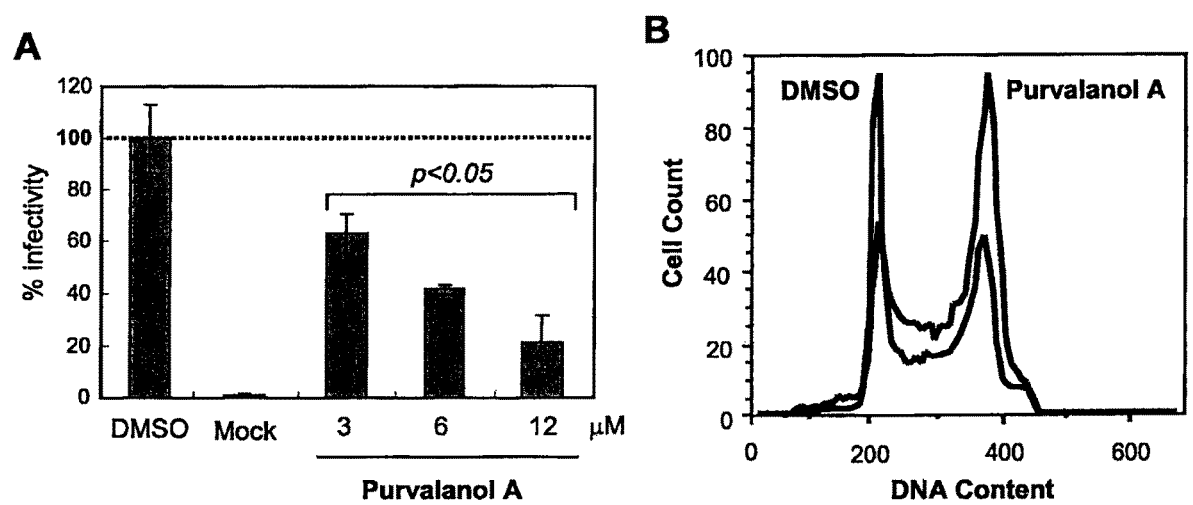
FIG. 6. Early M phase arrest by CDK1 inhibition interferes with HPV infection.

Cellular events in early prophase include nuclear envelope (NE) breakdown and changes in chromatin structure. Phosphorylation of NE components by CDK1 is critical for these events in early prophase (Collas, J. Cell Sci. (1999) 112:977-987; Peter et al., (1990) Cell 61:591-602; Santamaria et al., Nature (2007) 448:811-815). Thus, to examine whether entry into early prophase is critical for HPV infection, we tested hpvSEAP infection in the 293T cells treated with the known CDK1 inhibitor, purvalanol A (Gray et al., (1998) Science 281: 533-538). Purvalanol A inhibited HPV infection dose-specifically, with 12 μM both significantly arresting the cell cycle at G2/M phase and inhibiting HPV infection about 5-fold (FIGS. 6A and 6B). These results imply that cellular event(s) exclusively happening in early prophase are critical for HPV infection to deliver virions into the nucleus and early gene expression.

Figure 7:
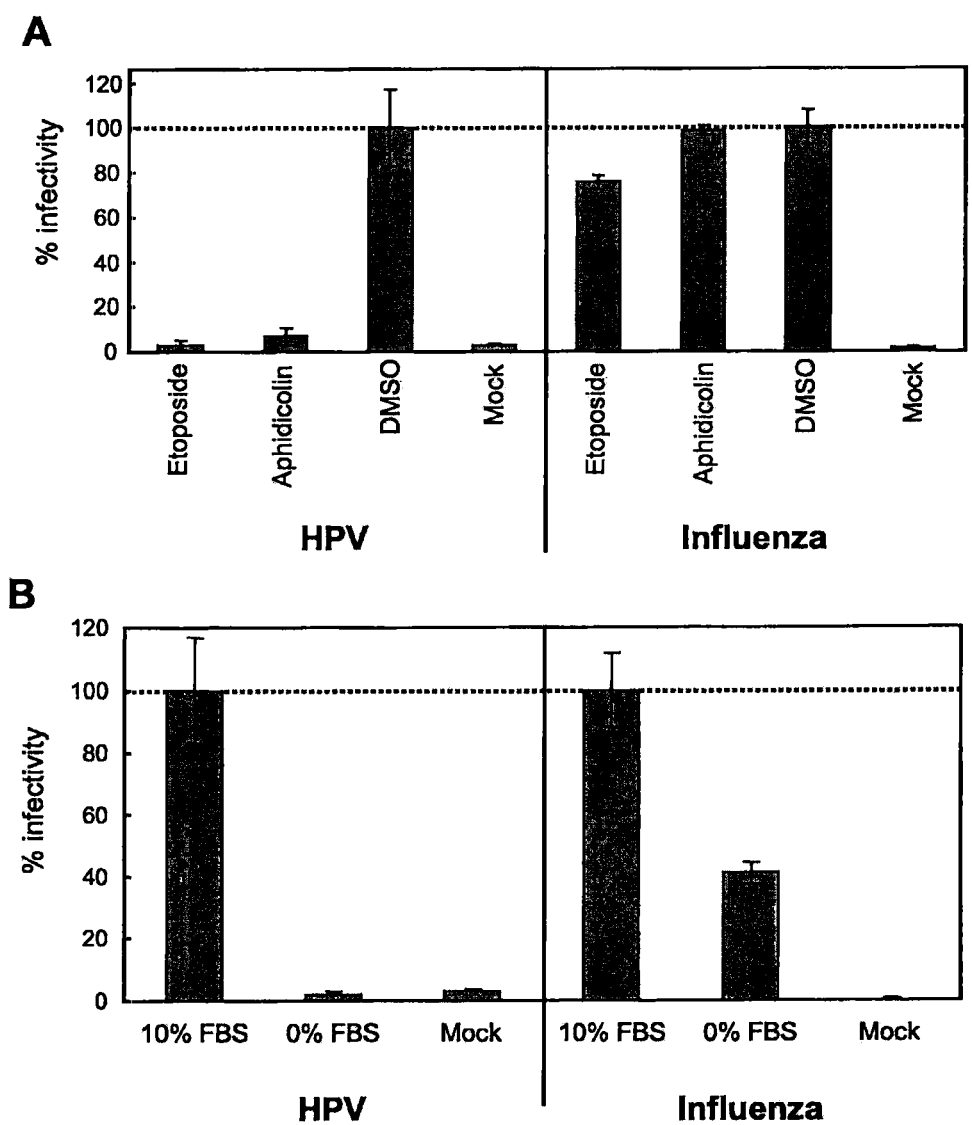
FIG. 7. Cell cycle arrest does not inhibit influenza virus.

Influenza virus genome delivery via nuclear pores is unaffected by cell cycle inhibitors that block HPV infection. HPV minor capsid protein L2 has nuclear localization signals, and, consequently, it has been hypothesized that L2 directs nuclear pore-mediated import of HPV DNA during infection (Fay et al., J. Virol (2004) 78:13447-13454). One virus that is well established to import its genome into intact nuclei via nuclear pores is influenza virus (Kemler et al., Virology (1994) 202:1028-1033; Neumann et al., J. Virol (1997) 71:9690-9700). To test whether HPV and influenza virus might share similar nuclear entry mechanisms, we treated 293T cells in parallel with either recombinant influenza virus or Renilla luciferase-expressing HPV pseudovirions in the presence and absence of etoposide and aphidicolin. While etoposide and aphidicolin efficiently blocked HPV infection, as before, they did not significantly affect influenza infection (FIG. 7A), showing that their effects on HPV could not be explained by effects on nuclear pores. We also observed in HaCaT cells the same difference in cell cycle dependency when those cells were arrested by serum and inoculated with the same Renilla luciferase-expressing HPV pseudovirions or recombinant influenza virus. Under these conditions (FIG. 7B), HPV infection was inhibited over 50 fold while influenza virus was only reduced approximately 2-fold, likely due to the general suppression of cell metabolism upon serum starvation.

Discussion

HPVs are clinically important pathogens due to their strong association with multiple human malignancies and because they are the most common sexually transmitted pathogens. Some oncogenic mechanisms of HPV are well known, especially pathways involved with E6 and E7 viral oncoproteins (Hebner et al., Rev. Med. Virol. (2006) 16: 83-97). However, many other basic mechanisms of the HPV life cycle are largely unknown including how HPV selectively effects only undifferentiated basal cells. Here, we define one of the bases for this restriction by showing that cell cycle progression into mitosis and, in particular, events in early prophase are critical for HPV early infection.

Viruses employ varied strategies to deliver their genetic material to the nucleus for replication and viral gene expression (Hebner et al., Rev. Med. Virol. (2006) 16: 83-97). While adenoviruses dissociate their capsids in the cytoplasm and import naked genomic DNA into the nucleus, herpesvirus virions release their genome into the nucleus without any extensive capsid disassembly, and polyomaviruses and parvoviruses transport the entire capsid into the nucleus. The nuclear import strategies of papillomaviruses have been largely unexplored, mainly because the means for producing high yields of infectious virus have only recently been attained (Buck et al., J. Virol. (2004) 78:751-757; Pyeon et al., Proc. Nat'l Acad. Sci. USA (2005) 102:9311-9316. Epub 2005 June 9315).

In the present study, using infectious wild type HPV16 virions, we found that events in the early prophase segment of mitosis are critical for establishing HPV infection, as assayed by introduction and expression of HPV-encapsidated DNA in the nucleus. As discussed below, these events could include nuclear envelope breakdown, cytoskeleton restructuring, and subnuclear structure changes as well as the specific expression of one or more genes or gene combinations in early mitosis.

One critical event in early phases of mitosis is nuclear envelope (NE) breakdown. This is triggered by a signal cascade that involves polo I like kinase 1 (plk1) and cyclin B1-associated CDK1 (Collas, J. Cell Sci. (1999) 112:977-987; Peter et al., Cell (1990) 61:591-602; Burkard et al., Proc. Nat'l Acad. Sci. USA (2007) 104:4383-4388. Epub 2007 March 4386). Using a chemical inhibitor of CDK1, purvalanol A (Gray et al., Science (1998) 281: 533-538), we found that CDK1 activity is required for efficient infection by HPVs (FIG. 6A). Therefore, our data are consistent with the hypothesis that NE breakdown is necessary for the HPV encapsidated DNAs to enter the nucleus. This is similar to the strategy thought to be employed by simple retroviruses to allow nuclear entry and integration of their proviral genomes (Bieniasz et al., Cell cycle dependence of foamy retrovirus infection. J. Virol. 69: 7295-7299 (1995); Lewis et al., J. Virol. (1994) 68: 510-516).

The process that initiates nuclear envelope breakdown is not fully understood. While the phosphorylation of NE components by CDK1 correlates with NE breakdown, and inhibition of cdk1 prevents NE breakdown [Collas, J. Cell Sci. (1999) 112:977-987; Peter et al., Cell (1990) 61:591-602), some have argued that NE breakdown is initiated by mechanical tension induced by spindle microtubules, leading to holes in the NE (Margalit et al., J. Cell Biochem. (2005) 95:454-465; Salina et al., Cell (2002) 108:97-107). Consistent with this hypothesis, the microtubule minus end motor, dynein, translocates to the outer face of the NE just before NE breakdown. This model for NE breakdown by mechanical tension has an interesting connection to HPV infection.

L2 binds to dynein and this is thought to allow L2:HPV DNA complexes to be translocated along microtubules towards the nucleus (Florin, J. Virol. (2006) 80:6691-6696). Thus the dynein-mediated trafficking of HPV encapsidated DNA cargo may not just contribute to movement of the encapsidated DNA to the intracytoplasmic destination of dynein, but microtubule organizing center, but might also contribute to nuclear localization if the above described model for NE breakdown is correct, as originally proposed Another notable cellular event in early mitosis is the reorganization of cytoplasmic microtubules to support mitotic spindle formation, chromosome segregation, and cell division (Hughes et al., PLoS Biol. (2008) 6:e98; Luders et al., Nat. Rev. Mol. Cell Biol. (2007) 8:161-167). Like many other viruses, HPV also utilizes microtubule structure to be delivered from cell surface to the nucleus (Florin, J. Virol. (2006) 80:6691-6696), although many details of this process remain to be understood. Our results are consistent with the possibility that effective HPV entry and/or HPV DNA delivery require cell cycle-associated reorganization of microtubules, such as the interaction of microtubules with host chromosomes in early mitosis.

In addition, restructuring of PML oncogenic bodies (PODs) and chromatin in early mitosis could be necessary for establishing HPV infection in the nucleus. PODs, also know as ND10, are multiple subnuclear bodies implicated in multiple cellular functions including transcription, DNA repair, viral defense, stress, cell cycle regulation, proteolysis and apoptosis (Borden, Mol. Cell Biol. (2002) 22:5259-5269; Ching et al., J. Cell Sci. (2005) 118:847-854). PODs are also the final destination of HPV DNA during the initial steps in infection and sites at or near which HPV DNA replication and transcription occur (Van Tine B. A., et al., J. Virol. (2004) 78:11172-11186; Day et al., Proc. Nat'l Acad. Sci. USA (2004) 101:14252-14257 Epub 12004 September 14221). PODs are dynamically restructured during S and M phases, responding to changes in chromatin organization (Bernardi et al., Nat. Rev. Mol. Cell Biol. (2007) 8:1006-1016). Thus, structural changes of PODs in early mitosis might be critical for HPV DNA localization to its POD destinations during the establishment of HPV infection. Other host mechanisms associated with chromatin structure in early mitosis might also contribute to structural changes of the incoming HPV DNA and thereby facilitate viral gene expression and replication inside the nucleus. Little is currently known about HPV chromatin structure and its contribution to viral gene expression.

Many genes such as polo-like kinases and aurora kinases are exclusively expressed only in early mitosis to certify completion of DNA replication, overcome mitotic checkpoint, and initiate mitosis (Ferrari, Cell Mol. Life Sci. (2006) 63:781-795). Beyond the potential mechanisms of cell cycle dependence suggested above, host genes or gene combinations specifically expressed only in early mitosis might have essential roles for HPV entry steps and/or HPV early gene expression.

HPV is thought to be able to infect the proliferating basal layer of the stratified epithelium only when wounds allow HPV to penetrate the physical barrier of upper skin layers. Wounding can also provide HPV particles access to laminin 5 or heparin sulfate moieties, both components of the extra cellular matrix (ECM) component of the epithelial basement membrane for which HPV particles have high affinity, thereby localizing the virus particles to basal surface epithelial cells it needs to infect (Culp T. D. et al., Virology (2006) 347:147-159 Epub 2005 December 2027; Culp T. D., et al., J. Virol. (2006) 80:8940-8950).

Laminin 5 is also the ECM partner of integrin α6/β4, which has been reported by some investigators to be an entry receptor for HPVs ((Culp T. D. et al, Virology (2006) 347:147-159 Epub 2005 December 2027; Culp T. D., et al., J. Virol. (2006) 80:8940-8950; Evander M. et al., J. Virol. (1997) 71:2449-2456). Our results suggest that wound healing might increase the efficiency with which the HPV DNA becomes established as a nuclear plasmid in the basal cells, because the basal cells are then in a hyperproliferative state (Werner S, et al., Science (1994) 266:819-822). HPV may also provide a mitogenic signal upon binding to cell surface receptors (Fothergill et al., Virology (2006) 352:319-328. Epub 2006 June 2015; Payne et al., J. Virol. (2001) 75:4150-4157), though if so, that signal is insufficient to overcome serum starvation-induced cell cycle arrest in HaCaT cells (FIGS. 2A and 2B). Regardless of why the cell is cycling, our data indicate that its movement through mitosis is a critical step in establishing HPV infection.

To further confirm physiological relevance regarding the cell cycle dependence of HPV infection, it would be necessary to examine these results in primary keratinocytes and in vivo models such as mouse and non-human primate. In addition, real-time particle imaging studies could be employed to identify what specific steps in infection are blocked upon cell cycle arrest; however, the ability to interpret accurately such imaging studies rests on the ability to distinguish particles leading to infectious events from the vast majority of particles that give rise to abortive or non-infectious events. To date no imaging method exists able to make such a distinction at the individual particle level.

The recent development of HPV vaccines offers an extremely important avenue for control of HPV infections and their associated cancers (Schiller J. J. Nat. Rev. Microbiol. (2004) 2:343-347). Nevertheless, due to limitations of recently approved HPV vaccines, there is an urgent need to identify other approaches to prevent HPV infections. One potentially valuable approach to prevent STDs including genital HPV infections could be ready access to effective microbicides (Howett et al., Curr. Pharm. Des. (2005) 11:3731-3746). From this perspective, our findings provide a new target mechanism for preventing initial HPV infection and blocking further spread. In addition, our chemical biology screening approach has successfully identified compounds that inhibit HPV infection, and the associated infection assay appears promising for large scale screening of compound libraries for development of further HPV preventives and therapeutics.

Experimental Procedures

Plasmids. pEF399, containing the complete W12E HPV16 genome (Flores et al., Virology (1999) 262:344-354), and all other plasmids used for virus packaging were previously described (Pyeon et al., Proc. Nat'l Acad. Sci. USA (2005) 102:9311-9316. Epub 2005 June 9315). pSEAP (pSEAP-control) for expression of secreted alkaline phosphatase (SEAP) was purchased from Clontech. pHPV16wpA-RL was cloned with HPV16 long control region (LCR, nucleotide position 7155-861), into pRL-null (Promega) to prepare a Renilla luciferase reporter system driven by native HPV16 promoter.

Cell lines. Human embryonic kidney cell line 293T from ATCC, and its enhanced SV40 T antigen-expressing daughter cell line 293TT (Buck et al., J. Virol. (2004) 78:751-757) from John Schiller, were maintained in Dulbecco's modified eagle's medium (DMEM) supplemented with 10% fetal bovine serum (FBS) (Invitrogen). Immortalized human keratinocyte cell line HaCaT (Boukamp et al., J. Cell Biol. (1988) 106:761-771) was maintained in F-media (Invitrogen, 3 parts F-12 and 1 part DMEM), supplemented with 10% FBS.

Production of virus particles. HPV virions and pseudovirions were prepared as described previously Pyeon et al., Proc. Nat'l Acad. Sci. USA (2005) 102:9311-9316. Epub 2005 June 9315]. Briefly, we cotransfected 293TT (provided by John Schiller) cells with HPV16 capsid protein expression plasmid as well as one of the target DNAs for encapsidation. After 48 hours at 37° C., cells were harvested and virions were purified using Optiprep gradient centrifugation. Influenza virus containing RL (Watanabe et al., J. Virol. (2003) 77:10575-10583) was provided by Yoshihiro Kawaoka.

Small molecule compounds and libraries. Known Bioactive Library (KBA01) consists of 3 commercially available collections totaling 4,160 compounds. KBA01 consists of 880 high purity compounds of known safety and bioavailability in humans of which over 85% are marketed drugs from Prestwick Chemical. The Prestwick compounds cover several therapeutic areas including neuropsychiatry, cardiology, immunology, inflammation, analgesia, etc.

Also included in the KBA01 library is 2000 diverse FDA approved drugs and natural products from Spectrum Chemical Collection From Microsource Discovery Systems, Inc. and 1280 compounds from the LOPAC of Sigma representing marketed drugs, failed development candidates and "gold standards" that have well-characterized activities. These compounds are the results of lead optimization efforts and have been rationally designed by structure-activity relationship studies. The NCI03 library consists of 235 natural products that were selected from the NCI open repository on the basis of structural diversity and availability of compound. Etoposide, Aphidicolin, Monastrol, 5-Fluorouracil, and CGP-74514A were purchased from Sigma.

High throughput screening. 293TT cells in 384-well plates were treated with 3.3 μM of library compounds for 4 hours and infected with hpvSEAP at 50 vge (viral genome equivalent)/cell for 48 hours. Culture supernatant 2.5 μl was used for virus infectivity assay using a Phospha-Light, a chemiluminescent alkaline phosphatase assay, (Applied Biosystems) and cell lysate was used for cell viability assay using CellTiter-Glo Luminescent cell viability assay (Promega). Biomek FX (Beckman Coulter) was used for automated liquid handling and a Victor 3-V plate reader (Perkin Elmer) was used for measuring luminescence. Screening was performed in the Small Molecule Screening Facility at the University of Wisconsin Comprehensive Cancer Center.

Infectivity assay. The activity of pSEAP-control-encapsidated pseudovirions (hpvSEAP) was measured using a Phospha-Light a chemiluminescent alkaline phosphatase assay (Applied Biosystems) and the activity of pHPV16wpA-RL-encapsidating pseudovirions (hpv16wpA-RL) was assayed using Renilla Luciferase Assay System (Promega). Infectivity of wild type HPV16 virions was examined by quantitative reverse transcriptase PCR (qRT-PCR) by amplifying viral mRNA signals from HPV16-treated 293TT cells. 293TT cells were infected with 50-100 vge/cell of packaged virus and incubated for 48 hours at 37° C.

Total RNA was isolated using the RNeasy total RNA purification kit (Qiagen), treated with RQ DNaseI (Promega) to remove possible DNA contaminants, purified again on RNeasy columns to remove DNaseI, and quantified by spectrophotometer. cDNA was synthesized from 20 μg of total RNA with oligo (dT) using a SuperScript cDNA synthesis kit (Invitrogen), and qPCR was performed with QuantiTect SYBR Green PCR Kit (Qiagen). Oligonucleotide primers (FIG. 3) were designed using the Primer3 primer design program (Rozen et al., In: Krawetz S, Misener S, editors. Bioinformatics Methods and Protocols: Methods in Molecular Biology. Totowa, N.J.: Humana Press. pp. 365-386 (2000)), synthesized by MWG and used at 0.5 μM for PCR amplification for 40 cycles of 30 second denaturation at 94° C., 30 seconds annealing at 55° C., and 30 seconds polymerization at 72° C. Obtained values were normalized with the levels of β-actin.

Flow cytometry. The cell cycle status of treated and untreated cells was analyzed using a propidium iodide (PI) incorporation method. Briefly, HaCaT cells were harvested, homogenized, fixed with cold 70% ethanol for 30 minutes at −20° C., and incubated with PI staining solution (1 mg/ml RNase A, 33 μg/ml PI, 0.2% NP-40 in PBS) for 30 minutes at room temperature. Stained cells were filtered through 35 μm-pore nylon mesh cell filtering caps (Falcon) and analyzed by flow cytometry using Becton Dickinson FACSCalibur (488 nm laser excitation).

We claim:

1. A method of inhibiting establishment of an initial sexually transmitted papovavirus infection in proliferating basal epithelial cells of an individual not infected with the papovavirus, comprising the step of:
   (a) selecting an individual not having the papovavirus infection;
   (b) administering to the individual a vulvovaginal or rectal formulation comprising an early prophase cell cycle inhibitor selected from the group consisting of etoposide, aphidicolin, and purvalanol prior to or at or around the time of sexual activity in an amount effective to inhibit the establishment of the papovavirus infection,
   wherein during administration the formulation is exposed to tissues or cells of a susceptible stratified epithelium of the individual prior to direct or indirect contact with cells infected by a papovavirus.

2. The method of claim 1, wherein the virus is human papillomavirus (HPV).

3. The method of claim 2, wherein the virus is high risk HPV.

4. The method of claim 3, wherein the virus is HPV16.

5. The method of claim 1, wherein the tissue or cells are selected from the group consisting of vulvovaginal tissues and cells and rectal tissue and cells.

6. The method of claim 1, wherein step (a) further comprises selecting an individual at risk for viral infection by direct or indirect contact of susceptible tissues or cells of the individual to the papovavirus through sexual activity.

7. The method of claim 1, wherein the vulvovaginal or rectal formulation comprises an effective amount of a spermicide.

8. The method of claim 1, further comprising inhibiting establishment of an initial infection at or around the time tissues or cells susceptible to viral infection are wounded.

9. The method of claim 1, wherein the vulvovaginal or rectal formulation is selected from the group consisting of a lubricant, cream, foam, gel, ointment, solution, lotion, jelly, tablet, lozenge, suppository, pessary, impregnated tampon, capsule, and implant.

10. The method of claim 1, wherein during the sexual activity the individual's tissues or cells directly or indirectly contact cells infected by the papovavirus.

11. The method of claim 1, wherein the formulation is administered directly to the vagina or rectum of the individual.

12. A method of inhibiting establishment of an initial high risk HPV infection in proliferating basal epithelial cells of an individual not infected with high risk HPV, comprising the step of:
   (a) selecting an individual not infected with high risk HPV;
   (b) administering to the individual a vulvovaginal or rectal formulation comprising an early prophase cell cycle inhibitor selected from the group consisting of etoposide, aphidicolin, and purvalanol immediately prior to or at or around the time of sexual activity in an amount effective to inhibit the establishment of an initial high risk HPV virus infection,
   wherein during administration the formulation is exposed to tissues or cells of a susceptible stratified epithelium.

13. The method of claim 12, wherein the high risk HPV is HPV16.

14. The method of claim 12, further comprising selecting an individual at risk for high risk HPV infection by direct or indirect contact of susceptible tissues or cells of the individual to the high risk HPV through sexual activity.

15. The method of claim 12, wherein during the sexual activity the individual's tissues or cells directly or indirectly contact cells infected by the high risk HPV.

16. The method of claim 12, wherein the tissue or cells are selected from the group consisting of vulvovaginal tissues and cells and rectal tissue and cells.

17. The method of claim 12, wherein the vulvovaginal or rectal formulation comprises an effective amount of a spermicide.

18. The method of claim 12, further comprising inhibiting establishment of an initial infection at or around the time tissues or cells susceptible to viral infection are wounded.

19. The method of claim 12, wherein the vulvovaginal or rectal formulation is selected from the group consisting of a lubricant, cream, foam, gel, ointment, solution, lotion, jelly, tablet, lozenge, suppository, pessary, impregnated tampon, capsule, and implant.

20. The method of claim 12, wherein the formulation is administered directly vulvovaginally, vaginally or rectally to the individual.

* * * * *

SEQUENCE LISTING

<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 1
aaatgacagc tcagaggagg ag                                              22

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 2
gagtcacact tgcaacaaaa gg                                              22

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 3
actatccagc gaccaagatc ag                                              22

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 4
tgttaaatgc agtgaggatt gg                                              22

```
<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 5
tttgtgtgct tttgtgtgtc tg                                              22

<210> SEQ ID NO 6
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 6
agaggctgct gttatccaca at                                              22
```